United States Patent [19]

Pedersen et al.

[11] Patent Number: 5,279,948

[45] Date of Patent: Jan. 18, 1994

[54] IMMOBILIZATION OF ENZYMES WITH A CROSS-LINKING AGENT AND A POLYMER CONTAINING L-AMINO ETHYLENE MOIETIES

[75] Inventors: Sven Pedersen, Gentofte; Ole B. Jørgensen, Koebenhavn, both of Denmark

[73] Assignee: Novo Nordisk A/S, Bagsvaerd, Denmark

[21] Appl. No.: 836,310

[22] PCT Filed: Nov. 23, 1990

[86] PCT No.: PCT/DK90/00305

§ 371 Date: Feb. 28, 1992

§ 102(e) Date: Feb. 28, 1992

[87] PCT Pub. No.: WO91/08287

PCT Pub. Date: Jun. 13, 1991

[30] Foreign Application Priority Data

Nov. 23, 1989 [DK] Denmark ............... 5893/89

[51] Int. Cl.⁵ .................. C12P 19/24; C12N 11/08; C12N 11/04
[52] U.S. Cl. .................... 435/94; 435/180; 435/182
[58] Field of Search ............ 435/180, 182, 94

[56] References Cited

U.S. PATENT DOCUMENTS 4,288,552 9/1981 Gestrelius ..................... 435/174
4,421,602 12/1983 Brunnmueller et al. ..... 526/303.1 X

FOREIGN PATENT DOCUMENTS

WO89/00195 1/1989 PCT Int'l Appl. .

OTHER PUBLICATIONS

Barta et al., Chemical Abstracts, vol. 107, p. 347 abstract No. 92712n (1987).
Yutaka Moroishi, abstract of JP 59-14789 (1984).

Primary Examiner—David M. Naff
Attorney, Agent, or Firm—Steve T. Zelson; Elias J. Lambiris

[57] ABSTRACT

Physically strong particles containing an immobilized enzyme are prepared for use in a fixed bed-column. The particles are prepared by adding a homopolymer of 1-amino ethylene or a copolymer of 1-amino ethylene and N-vinyl formamide to an aqueous medium containing an enzyme, adding a cross-linking agent to cross-link the enzyme and polymer and cause flocculation, and dewatering, sub-dividing and drying the resultant flocculant. Preferably, the enzyme is glucose isomerase and the cross-linking agent is glutaraldehyde, polyazetidine or diisocyanate.

25 Claims, No Drawings

IMMOBILIZATION OF ENZYMES WITH A CROSS-LINKING AGENT AND A POLYMER CONTAINING L-AMINO ETHYLENE MOIETIES

TECHNICAL FIELD

This invention relates to a particulate immobilized enzyme preparation, to use of the immobilized enzyme preparation in an enzyme-catalyzed process and to a process for immobilizing enzymatically active biological material.

BACKGROUND ART

It is known that enzymes can be immobilized without using a carrier by cross-linking with polyethylene imine (PEI) and a cross-linking agent such as glutaraldehyde or polyazetidine (e.g. U.S. Pat. No. 4,288,552, U.S. Pat. No. 4,355,105, EP 297,912). Such methods can be used to produce immobilized enzymes in particle form with good activity and physical strength, suitable for continuous use in a fixed-bed column. However, PEI is an expensive material, so it is desirable to find alternatives to this. Also, immobilization of some enzymes with PEI some times leads to poor flocculation, resulting in difficult dewatering.

It is the purpose of the invention to provide a method with improved flocculation and dewatering and without the need for PEI for producing an immobilized enzyme preparation with satisfactory properties for fixed-bed column use: activity, stability (half life) and physical strength (pressure drop).

SUMMARY OF THE INVENTION

It has surprisingly been found that the object can be obtained by replacing polyethyleneimine with a certain polymer that has never been described for use in immobilization.

Accordingly, the invention provides a particulate immobilized enzyme preparation obtainable by a process comprising the sequential steps of:
a) providing an aqueous medium containing enzymatically active biological material
b) adding a polymer containing 1-amino ethylene moieties and, optionally, N-vinyl formamide,
c) adding a cross-linking agent for amino groups,
d) holding the mixture to effect cross-linking and flocculation,
e) dewatering,
f) sub-dividing, and
g) drying.

The invention also provides use of the immobilized enzyme preparation in an enzyme-catalyzed process. Finally, the invention provides a process for immobilizing enzymatically active biological material, characterized by comprising the above sequential steps.

DETAILED DESCRIPTION OF THE INVENTION

The biological material to be immobilized according to the invention is enzymatically active. It may comprise enzymatically active microbial cells in the form of a culture broth containing intact cells or cell paste consisting of partly or fully disrupted cells. The biological material may also consist of or comprise a cell-free enzyme solution or purified enzyme.

The biological material may also comprise inactive protein, preferably 0–50% by weight. Thus, if highly purified enzyme is to be immobilized, it may be preferable to add inert protein such as albumin or gelatin.

The quantity of water present in the reaction mixture is not critical. Excess water will be removed during dewatering without any serious loss of active material. Thus, water may be added to obtain a convenient consistency. Conveniently, the biological material is added in the form of an aqueous dispersion or solution typically with 1–25% (w/w) of dry substance, particularly 1–10% in the case of culture broth or 10–25% in the case of a purified enzyme.

The polymer to be used in the invention may be a homopolymer of 1-aminoethylene or a copolymer of this monomer and N-vinyl formamide. It preferably contains 10–100 mole % (most preferably 25–50%) of —$CH_2$—$CH(NH_2)$— units and 0–90% mole % (most preferably 50–75%) of —$CH_2$—$CH(NH-CHO)$— units. It preferably has a molecular weight in the range 50,000–500,000. Such polymers may be produced by hydrolysis of N-vinylformamide homopolymer, e.g. according to U.S. Pat. No. 4,421,602 or EP 71,050. The molecular weight of the polymer is described in this application by the Fikentscher K value of the non-hydrolysed N-vinylformamide homopolymer as described in U.S. Pat. No. 4,421,602. This K value can vary between 10 and 200. The amount of polymer is preferably 2–30% by weight of the dry matter in the biological material and most preferably 2–15%.

Chitosan may be used in addition to the above-mentioned polymer. Preferably, 1–15% of chitosen and 1–15% of the polymer are used (% by weight of the dry matter in the biological material). The chitosan should be introduced before the addition of cross-linking in step c); it may be added together with the polymer.

The cross-linking agent used in the invention is one that reacts with amino groups. Examples are glutaraldehyde, diisocyanates (e.g. toluylene or hexamethylene diisocyanate) and polyazetidine (as described in EP 297,912).

Optionally, cross-linking agent may also be added to the aqueous medium of step a) and the mixture held sufficiently long to let partial cross-linking occur (e.g. 5–20 minutes) before introducing the polymer. In this case, the ratio of cross-linking agent added in step a) to that added in step c) is preferably 1:2–1:4.

The total amount of cross-linking agent is preferably in the range 5–40% by weight of the dry matter in the biological material. A relatively high amount, e.g. 20–40%, may be preferred in order to obtain physically strong particles; alternatively, a lower amount (e.g. 10–20%) may be used in order to obtain particles with less diffusion restriction and higher activity. The holding time in step d) is preferably 0.5–2 hours.

The temperature throughout the process is generally in the range 0°–60° C. Temperature near ambient is often convenient, but lower temperature may be needed due to enzyme instability.

pH throughout the process is generally around neutral, mostly between about 5 and about 9. Higher or lower pH may be preferred depending on the enzyme stability. A buffer may be included to stabilize pH during the reaction.

The dewatering step of the invention is intended to remove excess water after flocculation thereby generating a pasty mass. It is conveniently done by filtration or centrifugation.

Sub-dividing according to the invention is done to form the dewatered mass into individual particles of controlled size. A preferred technique is extrusion. Optionally, the extruded particles may be rounded (spheronized) before or after curing, e.g. by the "Marumerizer" technique disclosed in British patent specification GB 1,362,265.

The subdivided material is dried, e.g. to a water content below of 10–25% w/w. With an ultimate water content above 25% the microbial stability of the product may be unsatisfactory, and the particles may tend to aggregate over time in storage. Drying to a water content of below about 10% may inactivate the biological material. Preferred techniques are air drying or fluidized-bed drying, generally at 15°–80° C. In case of very sensitive biological materials, low temperature drying or freeze-drying may be needed.

The invention may be applied to immobilization of a wide range of enzymes. Some examples follow:

Glucose isomerase, e.g. derived from Streptomyces (especially *S. murinus*), Bacillus (especially *B. coagulans*) or Actinoplanes (especially *A. missouriensis*).

Aminopeptidase, e.g. derived from Pseudomonas

Penicillin acylase, e.g. derived from Fusarium.

Nitrilase, e.g. from Rhodococcus (especially *Rh. erythropolis*), from Pseudomonas or from Brevibacterium.

Fructosyl transferase, e.g. from Aspergillus.

Invertase, e.g. from Saccharomyces.

Lactase, e.g. from Kluyveromyces.

Cyanidase, e.g. from Alcaligenes.

EXAMPLES

EXAMPLE 1

A reference sample was prepared as follows:

1 l of glucose isomerase containing fermentation liquid from *Streptomyces murinus* (prepared according to U.S. Pat. No. 4,687,742, dry substance content 4%), was mixed with 10 g $MgSO_4 \cdot 7H_2O$ and pH adjusted to 7.5. 5 ml 50% glutaraldehyde was added and the cell sludge was stirred for 10 minutes under pH-adjustment to pH 7.5. Then 5.0% (on dry matter) of polyethylene imine (Sedipur, product of BASF, West Germany) was added and after thorough mixing 10 ml glutaraldehyde (total glutaraldehyde 18% based on cell sludge plus polyethylene imine dry substance) for cross-linking of the mixture. pH was constantly adjusted to 7.5. After 1 hour the cross-linked mixture was flocculated by addition of a cationic flocculant, Superfloc C 521 (Cyanamid Int.). The cross-linked enzyme was recovered by filtration, formed into particles by extrusion through a 0.8 mm screen and dried at room temperature.

A series of preparations according to the invention were made as described above, but with polyethyleneimine replaced by a polymer of 1-amino ethylene with or without N-vinyl formamide (experimental preparations from BASF, Germany). The composition of the polymers is shown in Table 1.

The glucose isomerase activity was measured by Novo Analysis Method F-855310 (available on request from Novo Nordisk A/S, Denmark). Both initial activity of the immobilized enzyme and in some cases the activity during several months of continuous isomerization in laboratory scale columns (60° C., pH 7.5) was measured. The activity decay is expressed by the half life, the time where the activity is equal to half of the initial activity.

The pressure drop was measured over a column with a diameter of 24 mm and an enzyme bed height of 4 cm (5 g enzyme). The solution, 45% glucose in demineralized water with 1 g $MgSO_4/l$, was pumped through the column at a rate of 40 g/min at 60° C. The pressure drop (in mm of liquid) describes the physical stability of the enzyme particle, i.e. a low pressure drop corresponds to a good physical stability.

The experimental results (initial activity, half life and pressure drop) are shown in Table 2.

TABLE 1

| Polymer | Mole % —$CH_2$—$CH(NH_2)$— | Molecular weight Mn g/mol | K value |
|---------|------|------|------|
| A | 67 | 4–5 × $10^5$ | 106 |
| B | 100 | 4–5 × $10^5$ | 106 |
| C | 32 | 2–3 × $10^5$ | 86 |
| D | 61 | 2–3 × $10^5$ | 86 |
| E | 95 | 2–3 × $10^5$ | 86 |
| F | 43 | 3–4 × $10^4$ | 32 |
| G | 61 | 3–4 × $10^4$ | 32 |
| H | 98 | 3–4 × $10^4$ | 32 |

TABLE 2

| Polymer | Glucose isomerase activity IGIU/g | Half life hours | Pressure drop g/$cm^2$ |
|---------|------|------|------|
| Reference | 350 | 2000 | 15 |
| A | 450 | 1000 | 50 |
| B | 300 | 2000 | 31 |
| C | 300 | 2200 | 11 |
| D | 350 | 2000 | >100 |
| E | 380 | 900 | 49 |
| F | 330 | 2000 | 26 |
| G | 340 | 1800 | 23 |
| H | 310 | 900 | 17 |

EXAMPLE 2

A series of preparation were made as in Example 1, except that the double amount of glutaraldehyde was used, i.e. 10 ml 50% glutaraldehyde before addition of polymer (or polyethyleneimine) and 20 ml after. The total amount of glutaraldehyde thus amounts to 36%.

The results are shown in Table 3.

TABLE 3

| Polymer | GI-activity IGIU/g | Pressure drop, g/$cm^2$ |
|---------|------|------|
| Sedipur | 220 | 4 |
| B | 200 | 4 |
| C | 290 | 6 |
| D | 260 | 5 |
| G | 240 | 2 |

EXAMPLE 3

A series of preparations were made as in Example 1, except that half of the amount of polyethylene imine or the polymer of 1-amino ethylene with or without N-vinyl formamide (2.5% on dry matter) was used. The results are shown in Table 4.

TABLE 4

| Polymer | GI-activity IGIU/g | Half-life hours | Pressure drop |
|---------|------|------|------|
| Sedipur | 500 | 1100 | 148 |
| B | 480 | — | 184 |
| C | 550 | 1100 | 356 |
| D | 540 | 1200 | 551 |
| G | 505 | — | 127 |

EXAMPLE 4

1 liter of glucose isomerase containing fermentaiton liquid from Streptomyces murinus (4% dry substance content) was mixed with 10 g $MgSO_4 \cdot 7H_2O$ and pH adjusted to 7.5. 15 ml 50% glutaraldehyde was added and the cell sludge was stirred for 10 minutes under pH-adjustment to pH 7.5. Then 2.5% (on dry matter) of polymer C and 2.5% (on dry matter) of chitosan (Kayamic 400, a product from Nippon Kayaku Co., Ltd.) dissolved in 460 ml 0.5% acetic acid was added and thoroughly mixed. pH was added and thoroughly mixed. pH was constantly adjusted to 7.5. After 1 hour the cross-linked mixture was flocculated by addition of a cationic flocculant, Superfloc C521 (Cyanamid Int.). The cross-linked enzyme was recovered by filtration, formed into particles by extrusion through a 0.8 mm screen and dried at room temperature.

The results were:
GI-activity IGIU/g: 450
Pressure drop: 89

EXAMPLE 5

A series of preparations were made as in Example 1 except that all the glutaraldehyde was added to the fermentation liquid before the polymer and that the glutaraldehyde concentration was varied.

The results are shown in Table 5.

TABLE 5

| Polymer | Glutaraldehyde concentration, % | GI-activity IGIU/g | Half-life hours | Pressure drop g/cm$^2$ |
|---|---|---|---|---|
| Sedipur | 18 | 275 | 2000 | 4 |
| Sedipur | 27 | 240 | 1800 | 4 |
| Sedipur | 36 | 200 | 1500 | 7 |
| C | 18 | 300 | 1700 | 13 |
| C | 27 | 270 | 1500 | 20 |
| C | 36 | 205 | 1600 | 16 |

The results of the examples show that according to the invention, samples with good activity, stability and physical strength, suitable for use in fixed-bed column, can be obtained with various compositions of polymer and with various amounts of glutaraldehyde. Preparations with particularly good stability and physical strength are obtained with polymer containing 25-50% 1-amino ethylene. Preparations with particularly good physical strength are obtained by using 30-40% glutaraldehyde.

We claim:

1. A particulate immobilized enzyme preparation obtained by a process comprising the sequential steps of:
   a) providing an aqueous medium comprising an active enzyme,
   b) adding a polymer selected from the group consisting of homopolymers of 1-amino ethylene and copolymers of 1-amino ethylene and N-vinyl formamide,
   c) adding a cross-linking agent for amino groups,
   d) holding the mixture to effect cross-linking of the enzyme and the polymer with the cross-linking agent, and flocculation to produce a flocculant,
   e) dewatering the flocculant,
   f) sub-dividing the dewatered flocculant, and
   g) drying the sub-divided flocculant.

2. The immobilized enzyme preparation according to claim 1, wherein said polymer is added in amount of 2-30% by weight of the dry matter in said aqueous medium.

3. The immobilized enzyme preparation according to claim 1, wherein said copolymer comprises 10 to 100 mole % of —$CH_2$—$CH(NH_2)$— units and less than 90 mole % of —$CH_2$—$CH(NH-CHO)$— units.

4. The immobilized enzyme preparation according to claim 1, wherein chitosan is added prior to the addition of the cross-linking agent in step c).

5. The immobilized enzyme preparation according to claim 1, wherein the cross-linking agent is glutaraldehyde, polyazetidine or a diisocyanate.

6. The immobilized enzyme preparation according to claim 1, wherein the process comprises the additional steps of:
   adding the same cross-linking agent used in step c) to the aqueous medium of step a) and
   holding to effect partial cross-linking of the enzyme with the cross-linking agent prior to the addition of the polymer in step b).

7. The immobilized enzyme preparation according to claim 1, wherein the cross-linking agent is added in an amount of 5-40% by weight of the dry matter in said aqueous medium.

8. The immobilized enzyme preparation according to claim 1, wherein said aqueous medium is an enzyme solution.

9. The immobilized enzyme preparation according to claim 1, wherein said aqueous medium comprises enzymatically active cells or a cell mass made by disruption of said cells.

10. The immobilized enzyme preparation according to claim 1, wherein said aqueous medium further comprises an enzymatically inactive protein.

11. The immobilized enzyme preparation according to claim 1, wherein the enzyme is a glucose isomerase.

12. The immobilized enzyme preparation according to claim 11, wherein the glucose isomerase is derived from a strain of Streptomyces.

13. A continuous process for the isomerization of glucose, comprising passing a glucose solution through a column containing a fixed bed of the immobilized glucose isomerase according to claim 11.

14. A process for producing an immobilized enzyme preparation, comprising the sequential steps of:
   a) providing an aqueous medium comprising an active enzyme,
   b) adding a polymer selected from the group consisting of homopolymers of 1-amino ethylene and copolymers of 1-amino ethylene and N-vinyl formamide,
   c) adding a cross-linking agent for amino groups,
   d) holding the mixture to effect cross-linking of the enzyme and the polymer with the cross-linking agent, and flocculation to produce a flocculant,
   e) dewatering the flocculant,
   f) sub-dividing the dewatered flocculant, and
   g) drying the sub-divided flocculant.

15. The process according to claim 14, wherein said polymer is added in an amount of 2-30% by weight of the dry matter in said aqueous medium.

16. The process according to claim 14, wherein said copolymer comprises 10 to 100 mole % of —$CH_2$—$CH(NH_2)$— units and less than 90 mole % of —$CH_2$—$CH(NH-CHO)$— units.

17. The process according to claim 14, wherein chitosan is added prior to the addition of the cross-linking agent in step c).

18. The process according to claim 14, wherein the cross-linking agent is glutaraldehyde, polyazetidine or a diisocyanate.

19. The process according to claim 14, wherein the process comprises the additional steps of:
adding the same cross-linking agent used in step c) to the aqueous medium of step a) and
holding to effect partial cross-linking of the enzyme to the cross-linking agent prior to the addition of the polymer in step b).

20. The process according to claim 14, wherein the cross-linking agent is added in an amount of 5–40% by weight of the dry matter in said aqueous medium.

21. The process according to claim 14, wherein said aqueous medium is an enzyme solution.

22. The process according to claim 14, wherein said aqueous medium comprises enzymatically active cells or a cell mass made by disruption of said cells.

23. The process according to claim 14, wherein said aqueous medium further comprises an enzymatically inactive protein.

24. The process according to claim 14, wherein the enzyme is a glucose isomerase.

25. The process according to claim 24, wherein the glucose isomerase is derived from a strain of Streptomyces.

* * * * *